United States Patent
Abraham et al.

(10) Patent No.: US 12,376,995 B2
(45) Date of Patent: Aug. 5, 2025

(54) PATIENT INTERFACES FOR COOLING EYE TISSUE

(71) Applicant: Alcon Inc., Fribourg (CH)

(72) Inventors: Mario Abraham, Burgthann (DE); Michael Wittnebel, Hirschaid (DE)

(73) Assignee: ALCON INC., Fribourg (CH)

( * ) Notice: Subject to any disclaimer, the term of this patent is extended or adjusted under 35 U.S.C. 154(b) by 319 days.

(21) Appl. No.: 17/945,867

(22) Filed: Sep. 15, 2022

(65) Prior Publication Data

US 2023/0103117 A1    Mar. 30, 2023

Related U.S. Application Data

(60) Provisional application No. 63/245,480, filed on Sep. 17, 2021.

(51) Int. Cl.
| | |
|---|---|
| *A61F 9/009* | (2006.01) |
| *A61B 18/00* | (2006.01) |
| *A61F 9/008* | (2006.01) |

(52) U.S. Cl.
CPC .......... *A61F 9/009* (2013.01); *A61F 9/00802* (2013.01); *A61F 9/00825* (2013.01); *A61B 2018/00029* (2013.01); *A61B 2018/00041* (2013.01); *A61F 2009/00872* (2013.01)

(58) Field of Classification Search
CPC . A61B 2018/00029; A61B 2018/00041; A61F 9/009; A61F 9/00802; A61F 9/00825; A61F 2009/00872
See application file for complete search history.

(56) References Cited

U.S. PATENT DOCUMENTS

| | | | | |
|---|---|---|---|---|
| 5,616,139 | A | * | 4/1997 | Okamoto ................ A61F 9/008 606/4 |
| 5,779,696 | A | * | 7/1998 | Berry ...................... A61F 9/008 606/5 |
| 2009/0137989 | A1 | * | 5/2009 | Kataoka .................. A61F 9/009 606/5 |
| 2020/0306080 | A1 | * | 10/2020 | Herekar .............. A61F 9/00821 |

FOREIGN PATENT DOCUMENTS

| | | |
|---|---|---|
| WO | 2006128038 A2 | 11/2006 |
| WO | WO-2019060756 A1 * 3/2019 ............. A61F 9/008 |
| WO | 2020093060 A2 | 5/2020 |

OTHER PUBLICATIONS

Wavelight® FS200 FS Femtosecond Laser, 2017, pp. 8-9, Novartis.

* cited by examiner

*Primary Examiner* — Tan-Uyen T Ho
*Assistant Examiner* — Cherie M Poland

(57) ABSTRACT

A patient interface for an ophthalmic laser system includes an interface portion and an attachment portion. The interface portion includes a transmissive portion and an interface wall. The transmissive portion allows a laser beam through to the cornea of an eye to perform an ophthalmic procedure. The interface wall is disposed outwardly from the transmissive portion. The attachment portion couples the interface portion to a region of the cornea to allow the laser beam through to the cornea to perform the ophthalmic procedure. The attachment portion also decreases the temperature of the region during the ophthalmic procedure.

22 Claims, 7 Drawing Sheets

PATIENT INTERFACES FOR COOLING EYE TISSUE

TECHNICAL FIELD

The present disclosure relates generally to patient interfaces for ophthalmic laser surgical systems, and more particularly to patient interfaces that cool eye tissue.

BACKGROUND

Ophthalmic laser surgery uses laser pulses to irradiate, shape, and/or cut tissue of the eye. During surgery, laser pulses are directed towards the eye. As the laser pulses hit a location of the eye, they increase the temperature at the location. If the temperature exceeds a damage threshold, the eye may suffer temporary or permanent damage. For example, the IEC standard 60601-1 sets 41° C. as the maximum temperature of the tissue. Accordingly, it is important to cool the tissue of the eye.

BRIEF SUMMARY

In certain embodiments, a patient interface for an ophthalmic laser system includes an interface portion and an attachment portion. The interface portion includes a transmissive portion and an interface wall. The transmissive portion allows a laser beam through to the cornea of an eye to perform an ophthalmic procedure, and the interface wall is disposed outwardly from the transmissive portion. The attachment portion couples the interface portion to a region of the cornea to allow the laser beam through to the cornea to perform the ophthalmic procedure. The attachment portion also decreases the temperature of the region during the ophthalmic procedure.

Embodiments may include none, one, some, or all of the following features: The attachment portion includes one or more channels, and decreases the temperature of the region by receiving fluid through the one or more channels to transfer heat away from the region. The attachment portion includes a receptacle configured to receive a cold core, and decreases the temperature of the region by allowing the cold core to transfer heat away from the region. The attachment portion includes a heat pump configured to transfer heat, and decreases the temperature of the region by transferring heat, with the heat pump, away from the region. The attachment portion has an annular shape that receives the interface wall of the interface portion to removably couple the interface portion to the attachment portion. The interface portion and the attachment portion formed as formed as one piece.

In certain embodiments, a patient interface for an ophthalmic laser system includes an interface portion and an attachment portion. The interface portion includes a transmissive portion and an interface wall. The transmissive portion allows a laser beam through to the cornea of an eye to perform an ophthalmic procedure. The transmissive portion also decreases the temperature of the region during the ophthalmic procedure. The interface wall is disposed outwardly from the transmissive portion. The attachment portion couples the interface portion to a region of the cornea to allow the laser beam through to the cornea to perform the ophthalmic procedure.

Embodiments may include none, one, some, or all of the following features: The transmissive portion includes first and second layers. The first layer transfers heat in a first direction. The second layer is disposed outwardly from the first layer, and transfers heat in a second direction substantially opposite to the first direction. The attachment portion includes one or more channels, and decreases the temperature of the region by receiving fluid through the one or more channels to transfer heat away from the region. The attachment portion includes a receptacle configured to receive a cold core, and decreases the temperature of the region by allowing the cold core to transfer heat away from the region. The attachment portion includes a heat pump configured to transfer heat, and decreases the temperature of the region by transferring heat, with the heat pump, away from the region. The attachment portion has an annular shape that receives the interface wall of the interface portion to removably couple the interface portion to the attachment portion. The interface portion and the attachment portion formed as formed as one piece.

In certain embodiments, a method for cooling a region of the cornea of an eye during an ophthalmic laser procedure includes coupling a patient interface outwardly from the region of the cornea for the ophthalmic laser procedure. The patient interface includes an interface portion and an attachment portion. The interface portion allows a laser beam through to the cornea to perform the ophthalmic laser procedure at the cornea. The attachment portion couples the interface portion to the region of the cornea. The method includes transferring, by the patient interface, heat away from the region of the cornea.

Embodiments may include none, one, some, or all of the following features: The interface portion of the patient interface transfers heat away from the region of the cornea. The attachment portion of the patient interface transfers heat away from the region of the cornea. The method further includes cooling at least a part of the patient interface prior to coupling the patient interface outwardly from the region of the cornea. The method further includes cooling the interface portion of the patient interface prior to coupling the patient interface outwardly from the region of the cornea. The method further includes cooling the attachment portion of the patient interface prior to coupling the patient interface outwardly from the region of the cornea.

In certain embodiments, a patient interface for an ophthalmic laser system includes an interface portion and an attachment portion. The interface portion includes a transmissive portion and an interface wall. The transmissive portion allows a laser beam through to the cornea of an eye to perform an ophthalmic procedure. The interface wall is disposed outwardly from the transmissive portion. The attachment portion couples the interface portion to a region of the cornea to allow the laser beam through to the cornea to perform the ophthalmic procedure. The attachment portion and interface portion decrease the temperature of the region during the ophthalmic procedure by: receiving fluid through one or more channels to transfer heat away from the region; comprising a receptacle that receives a cold core and allows the cold core to transfer heat away from the region; and/or comprising a heat pump that transfers heat away from the region.

BRIEF DESCRIPTION OF THE DRAWINGS

FIG. 6 shows a side view of a channel; FIGS. 7A, 7B, and 7C show top views of channels; and FIG. 7D shows a perspective view of a channel;

DESCRIPTION OF EXAMPLE EMBODIMENTS

Figure 1:
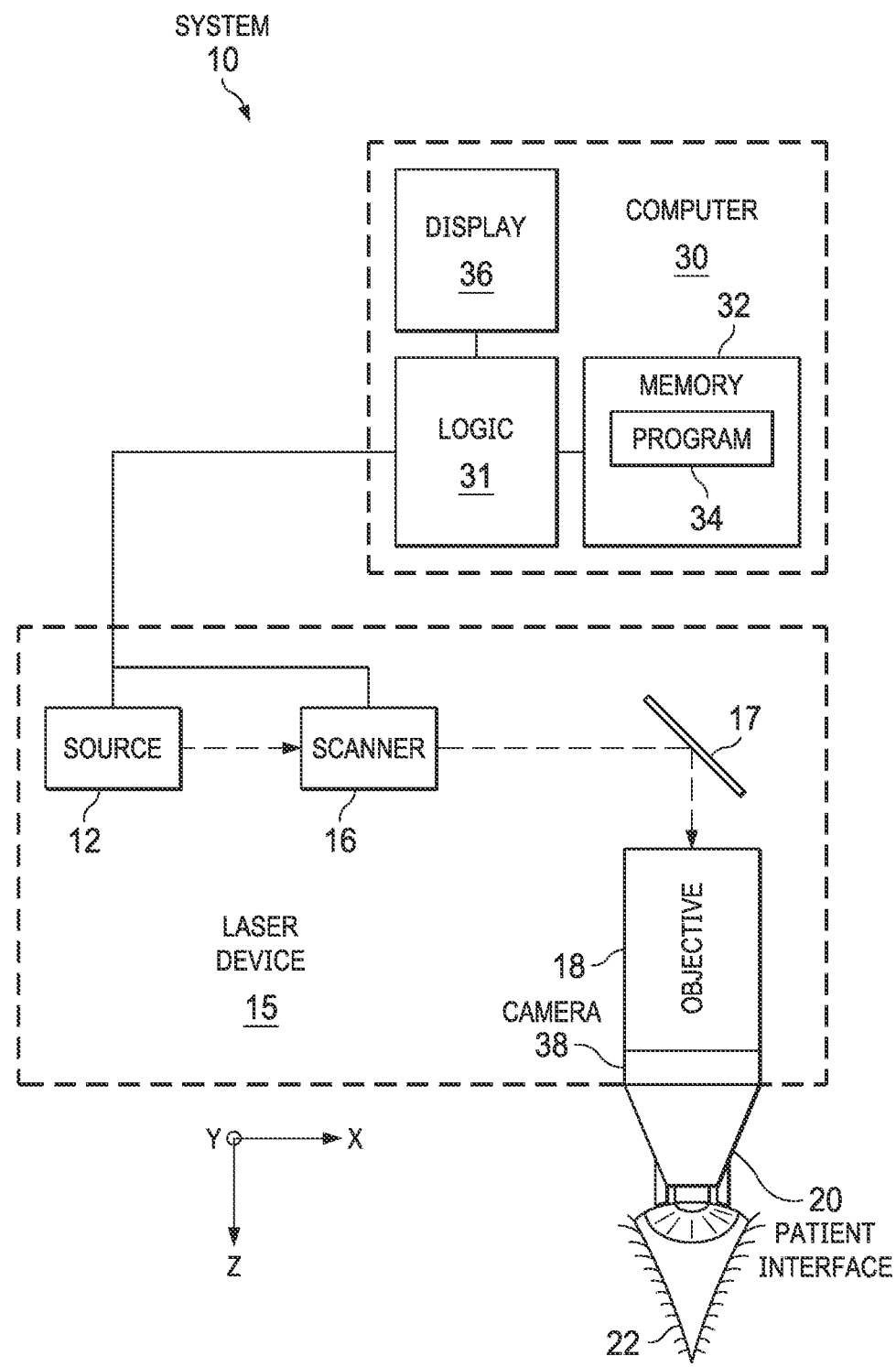
FIG. 1 illustrates an example of an ophthalmic surgical system with a patient interface that decreases the temperature of tissue at a surgical site of an eye, according to certain embodiments.

Referring now to the description and drawings, example embodiments of the disclosed apparatuses, systems, and methods are shown in detail. The description and drawings are not intended to be exhaustive or otherwise limit the claims to the specific embodiments shown in the drawings and disclosed in the description. Although the drawings represent possible embodiments, the drawings are not necessarily to scale and certain features may be simplified, exaggerated, removed, or partially sectioned to better illustrate the embodiments.

In certain embodiments, a patient interface can be used to cool eye tissue before, during, and/or after an ophthalmic procedure in order to avoid damaging the eye. In the embodiments, the patient interface includes an interface portion and an attachment portion. The interface portion allows a laser beam through to the cornea to perform an ophthalmic procedure, and the attachment portion couples the interface portion to the cornea. The interface portion and/or attachment portion may have structures that cool the cornea before, during, and/or after the ophthalmic procedure.

Cooling eye tissue with the patient interface may provide advantages in certain situations. First, the patient interface may provide flexibility to make adjustments in surgery parameters that increase tissue temperature. For example, the patient interface may allow for higher laser shot frequencies or pulse energies, which may decrease treatment time. As another example, temperature-related treatment pauses may possibly be reduced or omitted, which may avoid extending treatment time. Second, the patient interface may reduce temperature-related side effects and other problems, which may improve the safety and effectiveness of the treatment. Third, the patient interface may allow for treatment in more difficult ambient conditions, e.g., in non-air-conditioned areas in a very hot regions.

FIG. 1 illustrates an example of an ophthalmic surgical system 10 with a patient interface 20 that decreases the temperature of tissue at a surgical site of an eye 22, according to certain embodiments. In the illustrated example, system 10 includes a laser device 15, a patient interface 20, a camera 38, and a control computer 30, coupled as shown. Computer 30 includes logic 31, a memory 32 (which stores a computer program 34), and a display 36, coupled as shown. Laser device 15 includes controllable components, such as a laser source 12, a scanner 16, one or more optical elements 17, and a focusing objective 18, coupled as shown. Patient interface 20 is coupled as shown.

Turning to the parts of system 10, laser source 12 may be any suitable source that generates a laser beam, e.g., an excimer laser or an ultrashort pulse laser such as a femtosecond laser. An ultrashort pulse refers to a light pulse that has a duration less than a nanosecond, such as on the order of picoseconds, femtoseconds, or attoseconds. The laser beam may have any suitable wavelength, such as a wavelength in the range of 300 to 1500 nanometers (nm). In some embodiments, the focal point of the laser beam may create a laser-induced optical breakdown (LIOB) in tissue (e.g., corneal tissue) to yield a photodisruption in the tissue. In other embodiments, the focal point of the laser beam may ablate the tissue to remove portions of the tissue.

Scanner 16 transversely and longitudinally directs the focal point of the laser beam. The longitudinal direction refers to the direction of the laser beam propagation, also known as the z-direction. The transverse direction refers to directions orthogonal to the direction of beam propagation, also known as the xy-directions. Scanner 16 may transversely direct the laser beam in any suitable manner. For example, scanner 16 may include a pair of galvanometrically-actuated scanner mirrors that can be tilted about mutually perpendicular axes. As another example, scanner 16 may include an electro-optical crystal that can electro-optically steer the laser beam. Scanner 16 may longitudinally direct the laser beam in any suitable manner. For example, scanner 16 may include a longitudinally adjustable lens, a lens of variable refractive power, or a deformable mirror that can control the z-position of the beam focus. The components of scanner 16 may be arranged in any suitable manner along the beam path, e.g., in the same or different modular units.

One (or more) optical elements 17 direct the laser beam towards focusing objective 18. An optical element 17 can act on (e.g., transmit, reflect, refract, diffract, collimate, condition, shape, focus, modulate, and/or otherwise act on) a laser beam. Examples of optical elements include a lens, prism, mirror, diffractive optical element (DOE), holographic optical element (HOE), and spatial light modulator (SLM). In the example, optical element 17 is a mirror. Focusing objective 18 focuses the focal point of laser beam through the patient interface 20 towards a point of eye 22. In the example, focusing objective 18 is an objective lens, e.g., an f-theta objective.

Camera 38 records images of the movement of eye 22. Examples of camera 38 include a video, optical coherence tomography (OCT), or eye-tracking camera. Camera 38 delivers image data, which represent recorded images of the eye 22, to computer 30. Computer 30 may perform image processing on the image data to identify features of the eye to align the eye.

Computer 30 controls controllable components (e.g., laser source 12, scanner 16, optical elements 17, and/or focusing objective 18) in accordance with computer program 34. Computer program 34 includes computer code that instructs the controllable components to focus the laser beam at a region of the cornea and to photodisrupt at least a portion of the region.

Patient interface 20 interfaces with the cornea of eye 22 to couple eye 22 to laser device 15. Patient interface 20 serves to maintain eye 22 in place so the laser beam can treat eye 22. Patient interface 20 is described in more detail with reference to FIG. 2.

Figure 2:
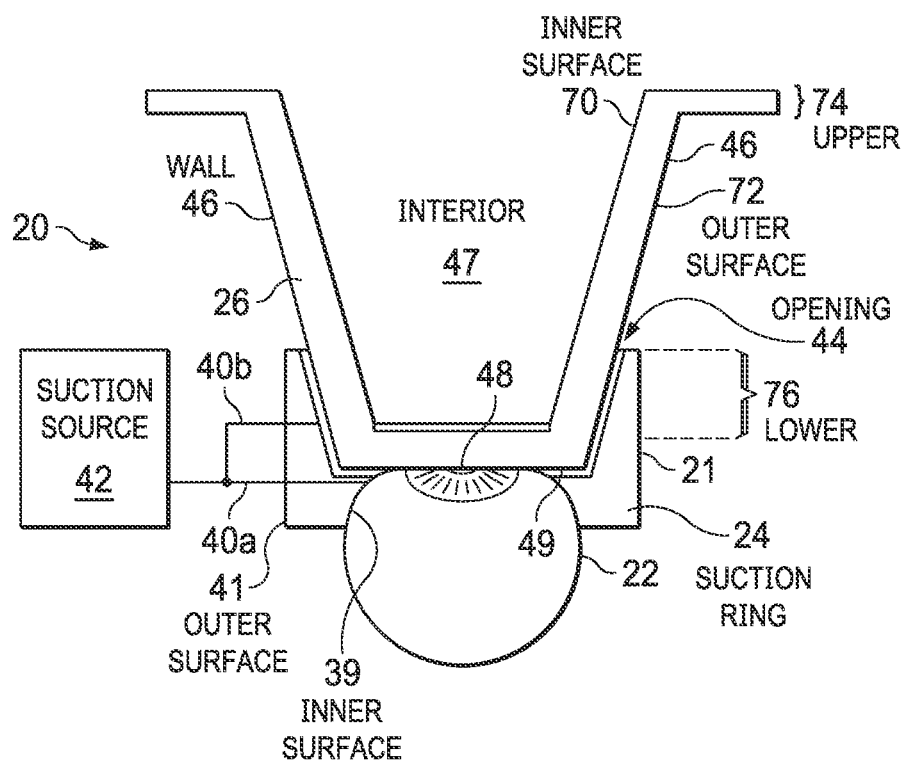
FIG. 2 illustrates an example of a patient interface that may be used to stabilize the position of an eye relative to the ophthalmic surgical system of FIG. 1, according to certain embodiments.

FIG. 2 illustrates an example of patient interface 20 that may be used to stabilize the position of eye 22 relative to ophthalmic surgical system 10 of FIG. 1, according to certain embodiments. In certain embodiments, patient interface 20 includes an attachment portion 21 and an interface portion 26. Interface portion 26 comes into contact with the cornea of eye 22, typically at the surgical site. Attachment portion 21 couples interface portion 26 to eye 22. Attachment portion 21 and interface portion 26 may be formed as one piece or may be formed as two or more separate pieces that can be removably coupled to each other.

Attachment portion 21 couples patient interface 20 to eye 22 in any suitable manner, e.g., via suction or mechanical attachment. In the example, attachment portion 21 comprises suction ring 24. Suction ring 24 has a substantially annular shape (e.g., perpendicular diameter axes are equivalent within a 20% or 10% deviation) with a ring axis, an inner surface 39, and an outer surface 41. Inner surface defines an opening 44. Suction ring 24 includes one or more evacuation channels 40 (40a, 40b) coupled to a suction source 42. Suction source 42 provides suction force. An evacuation channel 40 allows for suction to couple patient interface 20 to eye 22. In the example, the suction force through evacuation channel 40a affixes suction ring 24 to eye 22, and/or the suction force through evacuation channel 40b secures interface portion 26 to suction ring 24.

Interface portion 26 has a substantially frustoconical or cylindrical shape (e.g., perpendicular diameter axes are equivalent within a 20% or 10% deviation) with a conical or cylindrical axis and a cone wall 46 that defines a cone interior 47. Interface portion 26 is shaped to at least partially fit within opening 44. Cone wall 46 has an inner surface 70 and an outer surface 72, where inner surface 70 defines cone interior 47. Cone wall 46 has an upper portion 74 and a lower portion 76. Upper portion 74 typically couples patient interface 20 to system 10, and lower portion 76 includes or is coupled to contact portion 48. Contact portion 48 is translucent or transparent to the laser beam and has an abutment face 49 that comes into contact with the cornea of eye 22. Abutment face 49 is generally disposed outwardly from the surgical site. In certain embodiments, abutment face 49 is planar and forms a planar area on the cornea, which may define the xy-plane. In other embodiments, abutment face 49 is not planar, e.g., may be convex or concave.

Patient interface 20 has one or more structures that direct heat away from the cornea. The structures may have any suitable configuration. Examples of such structures include: (a) one or more channels that transport fluid that carries heat away from the cornea; (b) a cold core that transports heat away from the cornea; and (c) a heat pump that cools the cornea. In certain embodiments, attachment portion 21 may include one or more of the structures to decrease the temperature of the cornea. In other embodiments, interface portion 26 may include one or more of the structures to decrease the temperature of the cornea. In yet other embodiments, attachment portion 21 and interface portion 26 may include one or more of the structures to decrease the temperature of the cornea. Examples of the structures are described in more detail with reference to FIGS. 3 to 9.

Figure 3:
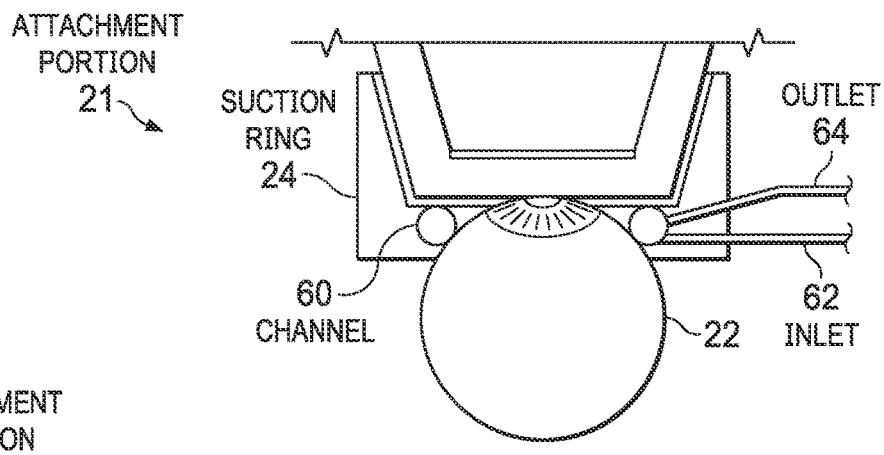
FIG. 3 illustrates an example of an attachment portion of the patient interface of FIG. 2 that transfers heat away from the cornea.

FIG. 3 illustrates an example of attachment portion 21 of patient interface 20 of FIG. 2 that transfers heat away from the cornea of eye 22. In the example, attachment portion 21 comprises suction ring 24 that has a channel 60 with an inlet 62 and an outlet 64. Channel 60 is disposed near eye 22 when suction ring 24 is affixed to eye. Channel 60 may have any suitable size or shape. In the example, channel 60 is annular, e.g., an annular ring, where the ring has an inner diameter equal to or slightly larger (e.g., 0 to 10 millimeters (mm)) than the inner diameter of suction ring 24. The path through channel 60 may have any suitable diameter, e.g., a diameter between 0 to 10 microns.

In an example of operation, channel 60 receives fluid through inlet 62. Any suitable biocompatible cooling or cooled fluid (e.g., liquid or gas) may be used, e.g., cooled water, saline solution, or other fluid; a compressed fluid; or a non-toxic refrigerant fluid. The fluid flows through channel 60 and out from outlet 64, transferring heat away from the cornea of eye 22.

Figure 4:
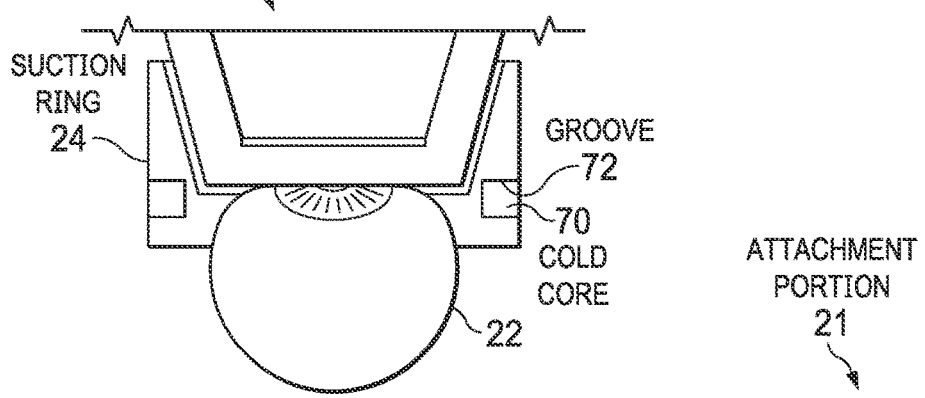
FIG. 4 illustrates another example of an attachment portion of the patient interface of FIG. 2 that transfers heat away from the cornea.

FIG. 4 illustrates another example of attachment portion 21 of patient interface 20 of FIG. 2 that transfers heat away from the cornea of eye 22. In the example, attachment portion 21 has a cold core 70 that can be cooled to transfer heat away from the cornea. Cold core 70 may comprise a biocompatible cooling or cooled material (e.g., liquid, gas, gel, or solid) that absorbs heat, e.g., the biocompatible cooling or cooled fluids listed with reference to FIG. 3 in liquid, gas, gel, or solid form; or a cooled metal or other solid. In some embodiments, cold core 70 may comprise a housing that houses the material.

Cold core 70 may have any suitable size or shape. In the example, a cold core 70 is annular with an inner diameter equal to or slightly larger than (e.g., 0 to 10 mm) the outer diameter of suction ring 24, such that cold core 70 can placed partially or completely into a receptable, such as a groove 72 of suction ring 24 of attachment portion 21. Cold core 70 may have a detachable portion that can be opened to increase the diameter of core 70 to fit around suction ring 26 and then closed to secure core 70 around suction ring 26. In an example of operation, groove 72 of suction ring 24 receives cold core 70, which transfers heat away from the cornea of eye 22.

Figure 5:
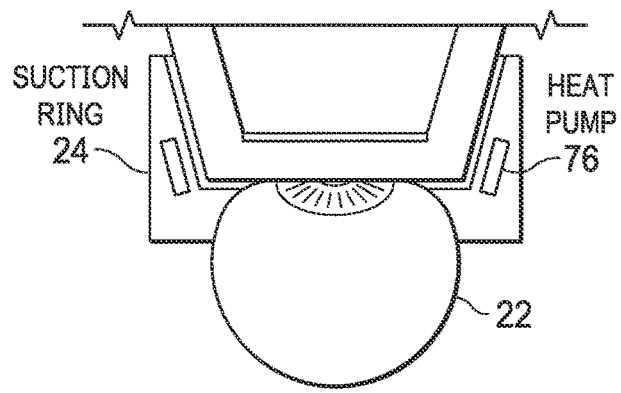
FIG. 5 illustrates another example of an attachment portion of the patient interface of FIG. 2 that transfers heat away from the cornea.

FIG. 5 illustrates another example of attachment portion 21 of patient interface 20 of FIG. 2 that transfers heat away from the cornea of eye 22. In the example, attachment portion 21 has a heat pump 76 that transfers heat away from the cornea of eye 22. Any suitable heat pump 76 may be used. Examples of heat pump 76 include a Peltier cooler, thermoelectric heat pump, or other solid-state active heat pump that transfers heat.

Figure 6:
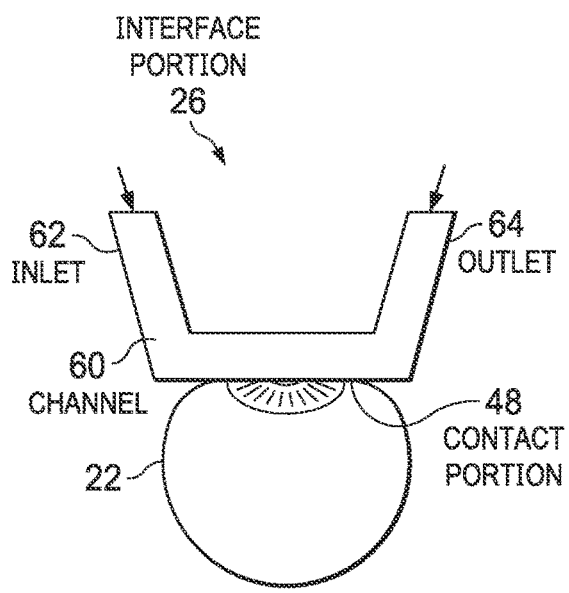
FIGS. 6, 7A, 7B, 7C and 7D illustrate examples of an interface portion of the patient interface of FIG. 2 that transfer heat away from the cornea.
Figure 7A:
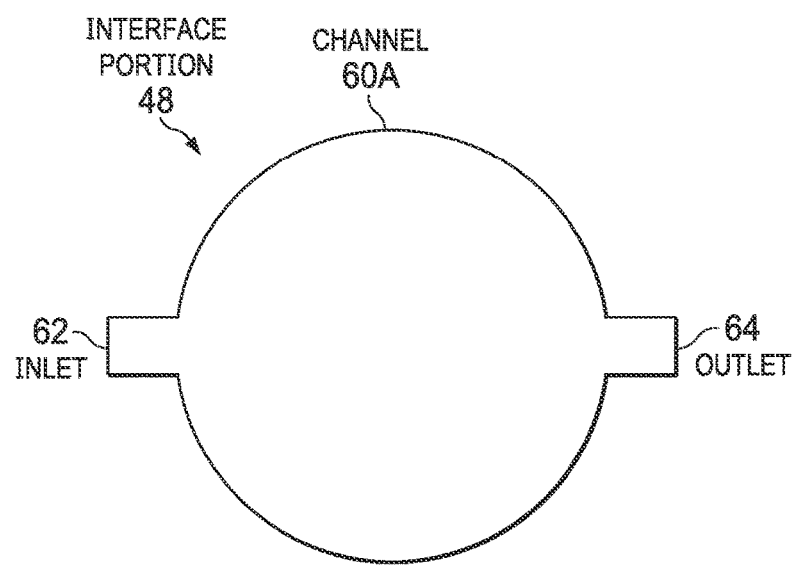
Figure 7B:
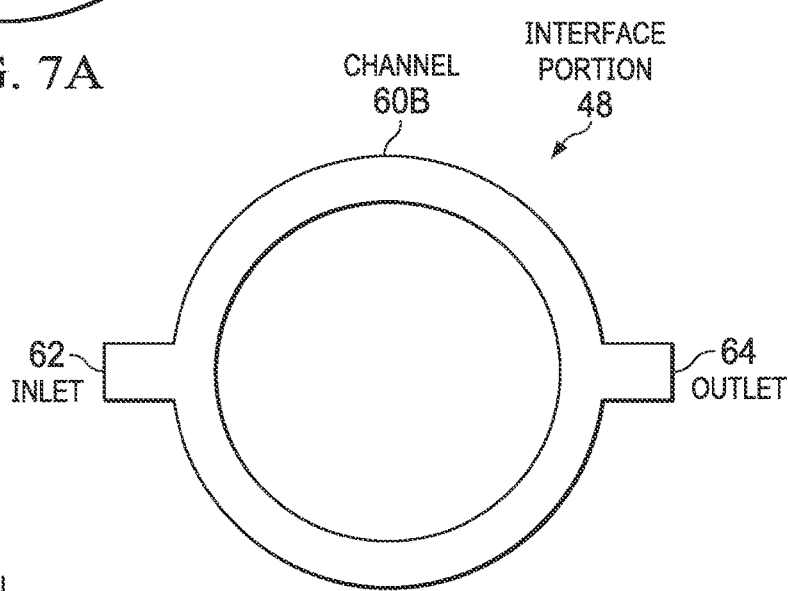
Figure 7C:
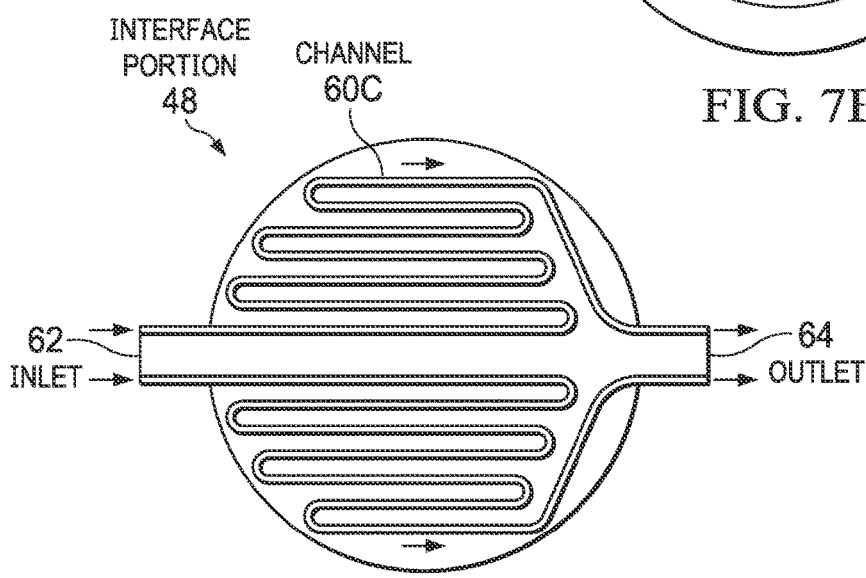
Figure 7D:
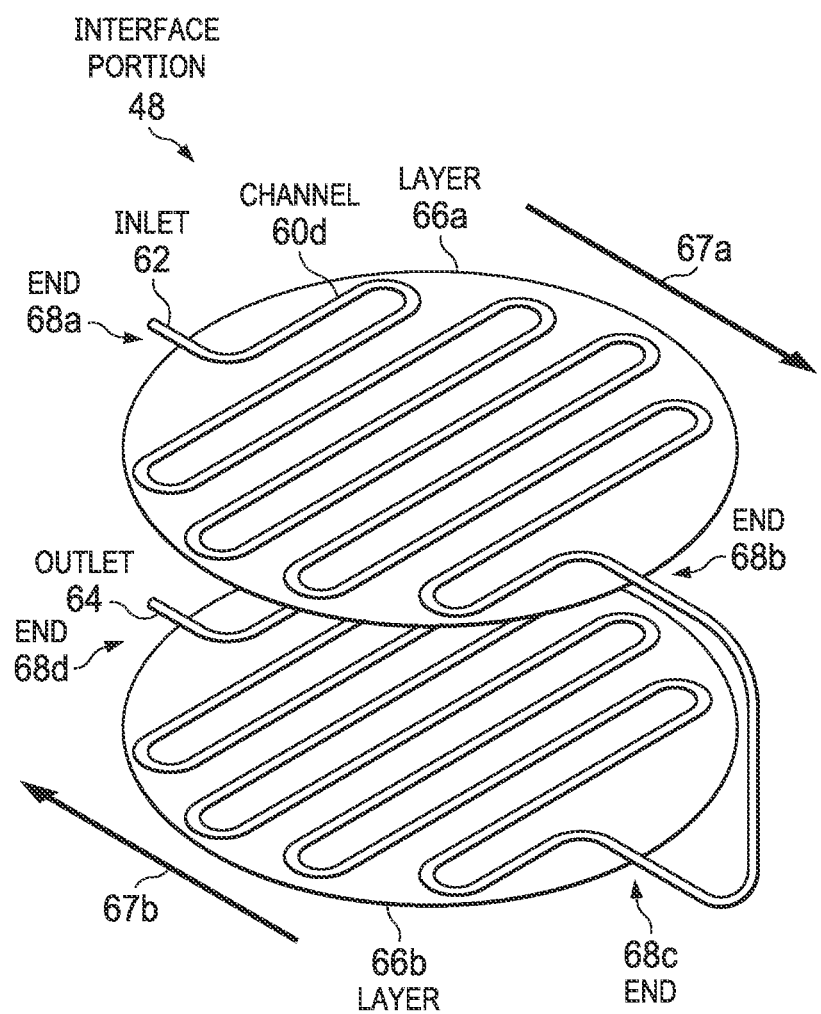

FIGS. 6 through 7D illustrate examples of interface portion 26 of patient interface 20 of FIG. 2 that transfer heat away from the cornea of eye 22. FIG. 6 shows a side view of channel 60; FIGS. 7A through 7C show top views of channels 60a, 60b, 60c; and FIG. 7D shows a perspective view of channel 60d. In the examples, interface portion 26 has a channel 60 (60a, 60b, 60c, 60d) with an inlet 62 and an outlet 64. Channel 60a is a chamber that may take up most (e.g., 75 to 90 or more than 90%) of the area of contact portion 48. Channel 60b has a plurality of paths from inlet 62 to outlet 64. The plurality of paths may have any suitable arrangement. In the illustrated example, two paths surround the area of contact portion 48. In other examples, one or more paths may cross through the area of contact portion 48.

Channel 60c exhibits a raster pattern through contact portion 48. A raster pattern scans an area in lines that travel from a first side of the pattern to an opposite side and then back to the first side. The raster pattern of channel 60c may have any suitable configuration. In the illustrated example, a path follows a raster pattern through approximately half the area of contact portion 48, and another path follows a raster pattern through approximately the other half. In another example, one path may follow a raster pattern through most (e.g., 75 to 90 or more than 90%) of the area. In yet another example, three or more paths may follow a raster pattern through most of the area. In yet another example, the lines may be closer together or farther apart.

Channel 60d is disposed within a plurality of layers 66 (66a, 66b) of contact portion 48. In the example, fluid enters layer 66a at an end 68a and exits at an end 68b (e.g., the opposite end) of layer 66a in a direction 67a. The fluid then enters layer 66b at an end 68c that is closer to end 68b of layer 66a and exits at an end 66d (e.g., the opposite end) of layer 66b that is closer to end 68a of layer 66a in a direction 67b that is substantially opposite to direction 67a (e.g., parallel within 40 degrees). Channel 60d is arranged such that cooler portion of layer 66a, near end 68a where the cooler fluid first enters, is disposed outwardly from the warmer portion of layer 66b, near end 68d where the warmer fluid exits, such that the cooler portion counteracts the warmer portion. Channel 60d may have any suitable pattern. In the example, channel 60d has a raster pattern, but may have any other suitable pattern, e.g., a pattern of channels 60a or 60b.

In an example of operation, channel 60 receives fluid through inlet 62. The fluid flows through channel 60, through contact portion 48 of interface 20, and out from outlet 64, transferring heat away from the cornea of eye 22. In the embodiments, channel 60 and/or the fluid may be in the path of the laser beam. Accordingly, design and/or operation of patient interface 20 and/or system 10 may need to take into account and compensate for how channel 60 and/or the fluid affect the laser beam. For example, the refractive indices of channel 60 and/or the fluid may need to be considered.

Figure 8:
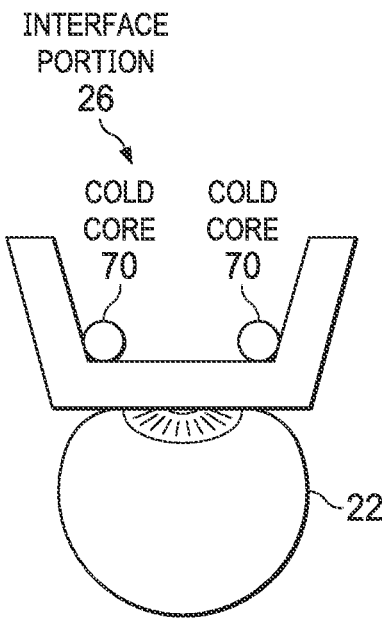
FIG. 8 illustrates another example of an interface portion of the patient interface of FIG. 2 that transfers heat away from the cornea.

FIG. 8 illustrates another example of interface portion 26 of patient interface 20 of FIG. 2 that transfers heat away from the cornea of eye 22. In the example, interface portion 26 has a cold core 70 placed outwardly from contact portion 48 of patient interface 20. Cold core 70 can be cooled to transfer heat away from the cornea. Cold core 70 may have any suitable size or shape. In the example, a cold core 70 is annular or circular with an outer diameter the equal to or slightly smaller than (e.g., 0 to 10 mm) the inner diameter of interface portion 26. In an example of operation, interface portion 26 receives cold core 70, which transfers heat away from the cornea of eye 22.

Figure 9:
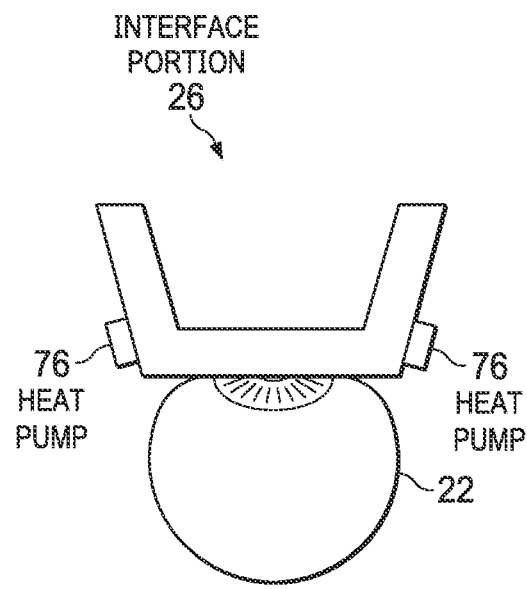
FIG. 9 illustrates another example of an interface portion of the patient interface of FIG. 2 that transfers heat away from the cornea.

FIG. 9 illustrates another example of interface portion 26 of patient interface 20 of FIG. 2 that transfers heat away from the cornea of eye 22. In the example, interface portion 26 has a heat pump 76 that transfers heat away from the cornea of eye 22. Heat pump 76 may be placed at or coupled to any suitable location of patient interface 20 (e.g., interface portion 26 and/or suction ring 24), such as a location where it does not interfere with the laser beam. In the example, heat pump 76 is coupled to interface portion 26, but not in contact with eye 22. In other examples, heat pump 76 may be placed where it is in contact with eye 22, such as coupled to a surface of patient interface 20 that is proximate to or touches eye 22. Any suitable heat pump 76 may be used, e.g., the heat pumps described with reference to FIG. 5.

Figure 10:
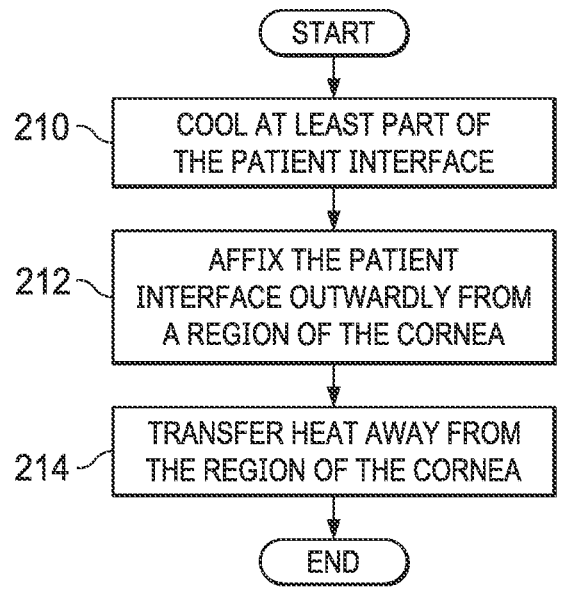
FIG. 10 illustrates an example of a method for cooling the cornea during an ophthalmic procedure that may be used with the patient interface of FIG. 2, according to certain embodiments.

FIG. 10 illustrates an example of a method for cooling the cornea during an ophthalmic procedure that may be used with patient interface 20 of FIG. 2, according to certain embodiments. The method begins at step 210, where at least part of patient interface 20 is cooled. The cooled part may be attachment portion 21 and/or interface portion 26. In certain embodiments, the part may comprise a biocompatible cooling or cooled material (e.g., liquid, gas, gel, or solid) that absorbs heat, e.g., the materials listed with reference to FIG. 4. Patient interface 20 is coupled outwardly from a region of the cornea at step 212. The cooled part of patient interface 20 transfers heat away from the region of the cornea at step 214 to cool the region. The method ends.

Figure 11:
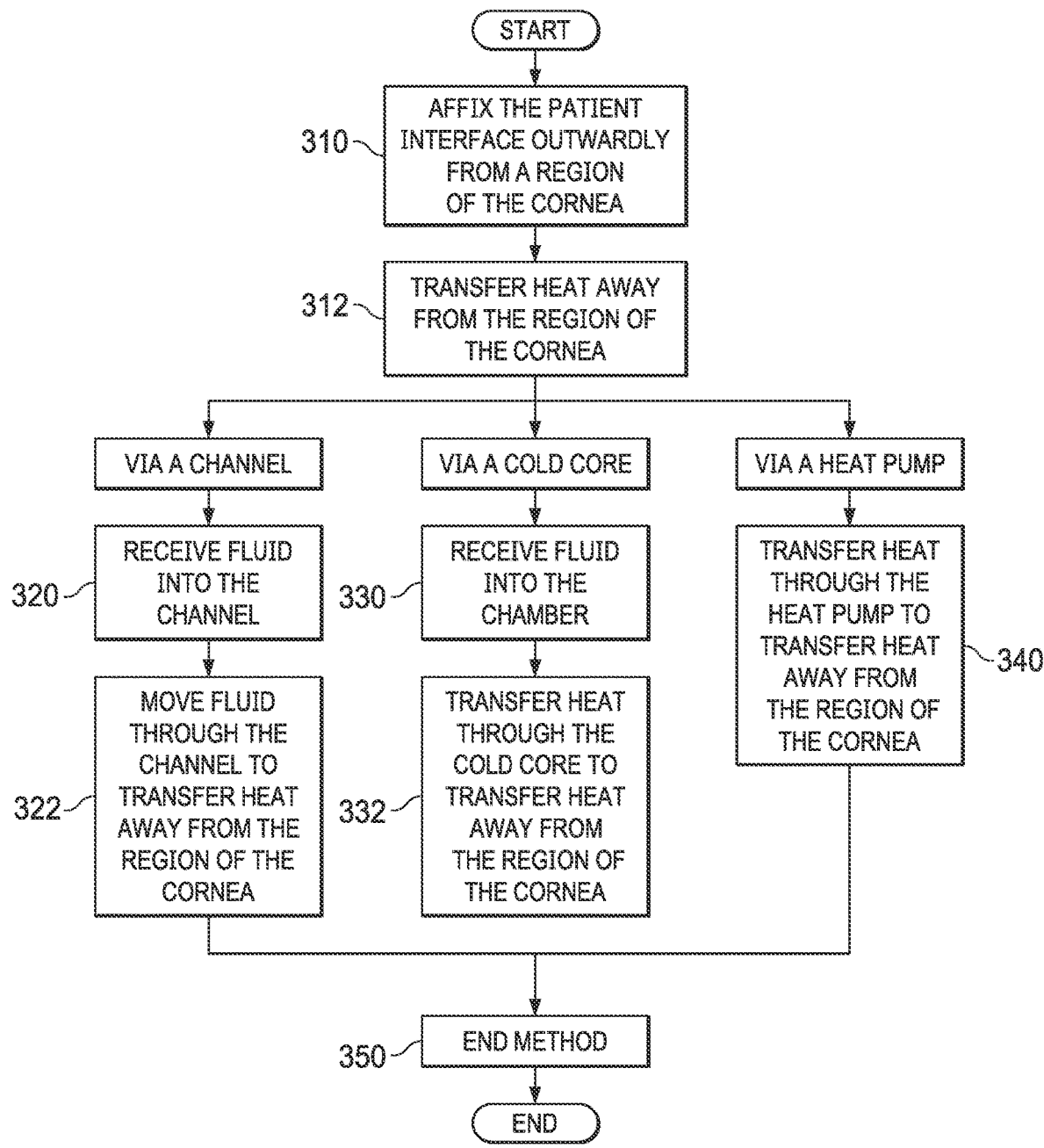
FIG. 11 illustrates another example of a method for cooling the cornea during an ophthalmic procedure that may be used with the patient interface of FIG. 2, according to certain embodiments.

FIG. 11 illustrates another example of a method for cooling the cornea during an ophthalmic procedure that may be used with patient interface 20 of FIG. 2, according to certain embodiments. The method begins at step 310, where patient interface 20 is coupled outwardly from a region of the cornea. Heat is transferred away from the region of the cornea at step 312. Depending on the type of patient interface 20, heat may be transferred via a channel, cold core, or heat pump.

Heat is transferred via a channel at steps 320 and 322. Patient interface receives fluid into the channel at step 320. The fluid is moved through the channel at step 322 to transfer heat away from the region. Heat is transferred via a cold core at steps 330 and 332. Patient interface receives a cold core into a chamber or groove at step 330. The cold core transfers heat away from the region at step 332. Heat is transferred via a heat pump at step 340. The heat pump transfers heat away from the region at step 340. After transferring heat, the method ends at step 350.

A component (such as computer 30) of the systems and apparatuses disclosed herein may include an interface, logic, and/or memory, any of which may include computer hardware and/or software. An interface can receive input to the component and/or send output from the component, and is typically used to exchange information between, e.g., software, hardware, peripheral devices, users, and combinations of these. A user interface is a type of interface that a user can utilize to communicate with (e.g., send input to and/or receive output from) a computer. Examples of user interfaces include a display, Graphical User Interface (GUI), touchscreen, keyboard, mouse, gesture sensor, microphone, and speakers.

Logic can perform operations of the component. Logic may include one or more electronic devices that process data, e.g., execute instructions to generate output from input. Examples of such an electronic device include a computer, processor, microprocessor (e.g., a Central Processing Unit (CPU)), and computer chip. Logic may include computer software that encodes instructions capable of being executed by an electronic device to perform operations. Examples of computer software include a computer program, application, and operating system.

A memory can store information and may comprise tangible, computer-readable, and/or computer-executable storage medium. Examples of memory include computer memory (e.g., Random Access Memory (RAM) or Read Only Memory (ROM)), mass storage media (e.g., a hard disk), removable storage media (e.g., a Compact Disk (CD) or Digital Video or Versatile Disk (DVD)), database, network storage (e.g., a server), and/or other computer-readable media. Particular embodiments may be directed to memory encoded with computer software.

Although this disclosure has been described in terms of certain embodiments, modifications (such as changes, substitutions, additions, omissions, and/or other modifications) of the embodiments will be apparent to those skilled in the art. Accordingly, modifications may be made to the embodiments without departing from the scope of the invention. For example, modifications may be made to the systems and apparatuses disclosed herein. The components of the systems and apparatuses may be integrated or separated, or the operations of the systems and apparatuses may be performed by more, fewer, or other components, as apparent to those skilled in the art. As another example, modifications may be made to the methods disclosed herein. The methods may include more, fewer, or other steps, and the steps may be performed in any suitable order, as apparent to those skilled in the art.

To aid the Patent Office and readers in interpreting the claims, Applicants note that they do not intend any of the claims or claim elements to invoke 35 U.S.C. § 112 (f), unless the words "means for" or "step for" are explicitly used in the particular claim. Use of any other term (e.g., "mechanism," "module," "device," "unit," "component," "element," "member," "apparatus," "machine," "system," "processor," or "controller") within a claim is understood by the applicants to refer to structures known to those skilled in the relevant art and is not intended to invoke 35 U.S.C. § 112 (f).

What is claimed:

1. A patient interface for an ophthalmic laser system, comprising:
   an interface portion comprising:
      a contact portion configured to allow a laser beam through to a cornea of an eye to perform an ophthalmic procedure; and
      an interface wall disposed outwardly from the contact portion; and
   an attachment portion comprising a suction ring, the attachment portion configured to:
      couple the interface portion to a region of the cornea of the eye to allow the laser beam through to the cornea to perform the ophthalmic procedure; and
      receive a cold core to decrease a temperature of the region during the ophthalmic procedure, the cold core comprising a detachable portion configured to:
         open to increase a diameter of the cold core to fit around the suction ring; and
         close to couple the cold core around the suction ring.

2. The patient interface of claim 1:
   the attachment portion comprising one or more channels; and
   the attachment portion configured to decrease the temperature of the region by receiving fluid through the one or more channels to transfer heat away from the region.

3. The patient interface of claim 1:
   the attachment portion comprising a receptacle configured to receive the cold core; and
   the attachment portion configured to decrease the temperature of the region by allowing the cold core to transfer heat away from the region.

4. The patient interface of claim 1:
   the attachment portion comprising a heat pump configured to transfer heat; and
   the attachment portion configured to decrease the temperature of the region by transferring heat, by the heat pump, away from the region.

5. The patient interface of claim 1, the attachment portion having an annular shape configured receive the interface wall of the interface portion to removably couple the interface portion to the attachment portion.

6. The patient interface of claim 1, the interface portion and the attachment portion formed as one piece.

7. The patient interface of claim 1:
   the suction ring having a groove; and
   the attachment portion configured to receive the cold core at the groove of the suction ring.

8. A patient interface for an ophthalmic laser system, comprising:
   an interface portion comprising:
      a contact portion comprising a plurality of layers comprising a channel configured to convey a fluid, the plurality of layers comprising:
         a first layer comprising a first entrance of the channel and a first exit of the channel, the channel configured to convey the fluid from the first entrance of the channel to the first exit of the channel; and
         a second layer disposed outwardly from the first layer, the second layer comprising a second entrance of the channel and a second exit of the channel, the channel configured to convey the fluid from the first exit of the channel to the second entrance of the channel, the channel configured to convey the fluid from the second entrance of the channel to the second exit of the channel, the contact portion configured to:
            allow a laser beam through to a cornea of an eye to perform an ophthalmic procedure at a region of the cornea; and
            convey the fluid through the channel to decrease a temperature of the region during the ophthalmic procedure; and
      an interface wall disposed outwardly from the contact portion; and
   an attachment portion configured to couple the interface portion to the region of the cornea of the eye to allow the laser beam through to the cornea to perform the ophthalmic procedure.

9. The patient interface of claim 8:
   the first layer configured to transfer heat in a first direction; and
   the second layer configured to transfer heat in a second direction, the second direction substantially opposite to the first direction.

10. The patient interface of claim 8:
    the attachment portion comprising one or more channels; and
    the attachment portion configured to decrease the temperature of the region by receiving fluid through the one or more channels to transfer heat away from the region.

11. The patient interface of claim 8:
    the attachment portion comprising a receptacle configured to receive a cold core; and
    the attachment portion configured to decrease the temperature of the region by allowing the cold core to transfer heat away from the region.

12. The patient interface of claim 8:
    the attachment portion comprising a heat pump configured to transfer heat; and
    the attachment portion configured to decrease the temperature of the region by transferring heat, by the heat pump, away from the region.

13. The patient interface of claim 8, the attachment portion having an annular shape configured receive the interface wall of the interface portion to removably couple the interface portion to the attachment portion.

14. The patient interface of claim 8, the interface portion and the attachment portion formed as one piece.

15. The patient interface of claim 8, the second entrance of the channel proximate to the first exit of the channel, the second entrance of the channel proximate to the first entrance of the channel.

16. A method for cooling a region of a cornea of an eye during an ophthalmic laser procedure, comprising:
coupling the patient interface of claim 8 outwardly from the region of the cornea for the ophthalmic laser procedure, the patient interface comprising an interface portion and an attachment portion, the interface portion configured to allow a laser beam through to the cornea to perform the ophthalmic laser procedure at the cornea, the attachment portion configured to couple the interface portion to the region of the cornea; and
transferring, by the patient interface, heat away from the region of the cornea.

17. The method of claim 16, the transferring, by the patient interface, heat away from the region of the cornea further comprising:
transferring, by the interface portion of the patient interface, heat away from the region of the cornea.

18. The method of claim 16, the transferring, by the patient interface, heat away from the region of the cornea further comprising:
transferring, by the attachment portion of the patient interface, heat away from the region of the cornea.

19. The method of claim 16, further comprising:
cooling at least a part of the patient interface prior to coupling the patient interface outwardly from the region of the cornea.

20. The method of claim 16, further comprising:
cooling the interface portion of the patient interface prior to coupling the patient interface outwardly from the region of the cornea.

21. The method of claim 16, further comprising:
cooling the attachment portion of the patient interface prior to coupling the patient interface outwardly from the region of the cornea.

22. A patient interface for an ophthalmic laser system, comprising:
an interface portion comprising:
a contact portion configured to allow a laser beam through to a cornea of an eye to perform an ophthalmic procedure; and
an interface wall disposed outwardly from the contact portion; and
an attachment portion configured to couple the interface portion to a region of the cornea of the eye to allow the laser beam through to the cornea to perform the ophthalmic procedure,
the attachment portion and the interface portion configured to decrease the temperature of the region during the ophthalmic procedure by performing one of the following:
the attachment portion and the interface portion configured to receive fluid through one or more channels to transfer heat away from the region;
the attachment portion and the interface portion comprising a receptacle configured to receive a cold core and to allow the cold core to transfer heat away from the region, the cold core comprising a detachable portion configured to open to increase a diameter of the cold core to fit around a suction ring of the attachment portion and to close to couple the cold core around the suction ring; and
the attachment portion and the interface portion comprising a heat pump and configured to transfer heat, by the heat pump, away from the region.

* * * * *